(12) United States Patent
Frenzel et al.

(10) Patent No.: US 7,256,153 B2
(45) Date of Patent: Aug. 14, 2007

(54) CARRIER CATALYTIC CONVERTER FOR THE SELECTIVE HYDROGENATION OF ALKINES AND DIENES

(75) Inventors: Andrea Frenzel, Limburgerhof (DE); Michael Hesse, Worms (DE); Andreas Ansmann, Wiesloch (DE); Ekkehard Schwab, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 670 days.

(21) Appl. No.: 10/148,798

(22) PCT Filed: Dec. 6, 2000

(86) PCT No.: PCT/EP00/12283

§ 371 (c)(1),
(2), (4) Date: Jun. 5, 2002

(87) PCT Pub. No.: WO01/41922

PCT Pub. Date: Jun. 14, 2001

(65) Prior Publication Data
US 2003/0023121 A1    Jan. 30, 2003

(30) Foreign Application Priority Data
Dec. 8, 1999  (DE) .................... 199 59 064

(51) Int. Cl.
B01J 21/08  (2006.01)
B01J 23/44  (2006.01)
B01J 23/50  (2006.01)

(52) U.S. Cl. ............... 502/243; 502/244; 502/245; 502/262; 502/250

(58) Field of Classification Search ........ 502/243, 502/244, 245, 262, 250, 330, 331
See application file for complete search history.

(56) References Cited

U.S. PATENT DOCUMENTS

| | | | |
|---|---|---|---|
| 4,247,725 A * | 1/1981 | Ohmori et al. ............. | 585/259 |
| 4,409,410 A | 10/1983 | Cosyns et al. ............. | 585/259 |
| 5,489,565 A | 2/1996 | Cheung et al. ............. | 502/325 |
| 5,648,576 A | 7/1997 | Nguyen Than et al. ..... | 585/260 |
| 5,856,262 A | 1/1999 | Flick et al. ................ | 502/328 |
| 6,015,769 A * | 1/2000 | Wang ........................ | 502/331 |
| 6,054,409 A | 4/2000 | Nguyen Thanh et al. ... | 502/330 |
| 6,127,310 A * | 10/2000 | Brown et al. .............. | 502/339 |
| 6,204,218 B1 | 3/2001 | Flick et al. ................ | 502/243 |
| 6,350,717 B1 | 2/2002 | Frenzel et al. ............. | 502/330 |
| 6,358,882 B1 * | 3/2002 | Salem et al. ............... | 502/305 |
| 6,420,308 B1 * | 7/2002 | Khanmamedova .......... | 502/344 |

FOREIGN PATENT DOCUMENTS

| | | |
|---|---|---|
| DE | 2 156 544 | 6/1973 |
| DE | 31 19 850 | 2/1982 |
| DE | 19 839 459 | 3/2000 |
| DE | 198 40 372 | 3/2000 |
| DE | 198 40 373 | 3/2000 |
| EP | 0 064 301 | 11/1982 |
| EP | 0 686 615 | 12/1995 |
| EP | 0 764 463 | 3/1997 |
| EP | 0 780 155 | 6/1997 |
| EP | 0 839 573 | 5/1998 |
| GB | 1 407 434 | 9/1975 |
| WO | WO98/37966 | 9/1998 |

* cited by examiner

Primary Examiner—Elizabeth D. Wood
(74) Attorney, Agent, or Firm—Novak Druce & Quigg, LLP

(57) ABSTRACT

A catalyst for the selective hydrogenation of alkynes and dienes in C2-C5+-olefin mixtures is described.

These catalysts contain
(a) a metal of the tenth group of the Periodic Table,
(b) a metal of the eleventh group of the Periodic Table and
(c) if required, a compound of a metal of the first or second group of the Periodic Table, these metals being applied to a support which is selected from the group consisting of silica, titanium dioxide, zirconium oxides, spinels, zinc aluminates, zinc titanates or mixtures of these substances, and the metal of the eleventh group being distributed homogeneously over the cross section of the catalyst particle and the metal of the tenth group being present in the edge layer close to the surface of the catalyst particle. Such a catalyst is prepared by applying the metal of the eleventh group, preferably during the preparation of the support itself, by impregnation with a solution of a suitable metal salt.

11 Claims, No Drawings

CARRIER CATALYTIC CONVERTER FOR THE SELECTIVE HYDROGENATION OF ALKINES AND DIENES

The present invention relates to the area of catalysis. More precisely, the present invention relates to a novel hydrogenation catalyst which makes it possible selectively to hydrogenate more highly unsaturated hydrocarbons, such as acetylenes and dienes, in olefin mixtures which were obtained by the crack process. The present invention furthermore relates to a process for the preparation of such a catalyst and a process for the selective hydrogenation of alkynes and dienes in olefin mixtures with the aid of such a catalyst.

Olefins are generally produced industrially in crack processes, for example by steam cracking or catalytic cracking by FCC. Specific mineral oil distillates are heated to temperatures of about 900° C., at which olefins form from the alkanes present. The crude mixture obtained is then separated by distillation, the fractions being cut in such a way that the C2 to C5$^+$-olefins are separated from one another. The olefins obtained are then used in further processing. Under the cracking conditions, however, alkynes (acetylenes) and dienes also form, the amounts of which depend on the process and on the experimental conditions chosen. However, these alkynes and dienes frequently present problems during further processing and storage. This is due on the one hand to a tendency to oligomerize and polymerize. Thus, products which frequently have to be removed from the product of further processing may be formed during the further processing. On the other hand, the alkynes and dienes have a strong tendency to form complexes. This presents problems in particular when the olefins are subjected to a catalytic process in the further processing step. The alkynes or dienes may then react with the catalyst and deactivate it or change the activity, which of course is undesirable.

For example, in this C2 cut which contains ethylene, acetylene is present as an undesired byproduct. Ethylene is further processed catalytically in large amounts to give polyethylene. Ethylene used for such a polymerization may generally have only an acetylene content of less than about 1 ppm. The same also applies to the C3 stream, which also contains propadiene (allene) and propyne in addition to propene. Propene, too, is further processed catalytically in a process which is similar to that of ethylene in a large amount to give polypropene. A propene which can be used for the polymerization may generally contain only less than about 10 ppm of allene and propyne.

In the other cuts of the crack process, too, products which are undesirable for the purposes of further processing form. Depending on the integration into the profitability chain, in the C4 cut vinyl acetylene, an impurity, is hydrogenated before the butadiene extraction. Alternatively, butadiene can be specifically converted into butene, such a refinement of the C4 stream being desired. The C5$^+$ cut contains cyclic pentenes and pentadiene, which should be converted into products which present no problem, linear C5 building blocks and the unsaturated C5$^+$ components being obtained.

A process for removing said byproducts is the selective hydrogenation of these alkynes and dienes. The impurities are converted in the further processing into components which present no problems or preferably into the desired product of the hydrocarbon fraction. The main problem in such a process is that, on the one hand, the catalyst used must have sufficient activity completely to hydrogenate the byproducts, which indeed are present only in relatively small amounts compared with the olefin, and thus to force the content of impurities to values which are tolerable in the further processing. When it is considered that in some cases a content of impurities of less than 1 ppm has to be reached, as is the case for polyethylene, it will be clear that the catalyst used in the selective hydrogenation must have a very high activity.

On the other hand, such a catalyst must also have a very high selectivity or, in other words, a low specific activity with respect to the olefin to be further processed, so that this is not hydrogenated or is hydrogenated only to a very small extent even to the corresponding alkane and is no longer available.

Furthermore, the catalysts used in the selective hydrogenations should also have the property of not catalyzing the oligomerization of alkynes and dienes. In fact, this reaction results in the formation of oily residues which accumulate on the catalyst. Deactivation of the catalyst is the result, which can occur even after less than one month, depending on the amount of byproducts formed.

According to the process described in the prior art, the selective hydrogenation is generally carried out using catalysts fixed on supports and comprising metals which are generally used in hydrogenations, mainly heterogeneous catalysts of the tenth group of the Periodic Table, i.e. Ni, Pd and Pt. In most cases, Pd is employed.

The support used is generally a porous inorganic oxide, for example silica, aluminosilicate, titanium dioxide, zirconium dioxide, zinc aluminate, zinc titanate, spinels and/or mixtures of such supports; generally, however, alumina or silica is used. Furthermore, promoters or other additives may be present. Processes for the selective hydrogenation of unsaturated compounds in hydrocarbon streams which contain them are known both in the form of liquid-phase hydrogenation or mixed gas/liquid-phase hydrogenation, by the trickle-bed or liquid-phase procedure, and in the form of pure gas-phase hydrogenation.

To be able to achieve the desired selectivity, said catalysts are modified. It is generally known that the desired increases in selectivity in the case of the abovementioned metals can be frequently achieved by adding CO during the hydrogenation. However, this requires special safety measures owing to the toxicity of the CO. In addition, this results in a CO-containing product which, for some further uses, first has to be purified to remove CO.

The prior art contains a large number of references which describe the use of supported palladium catalysts, which were modified by addition of promoters, in selective hydrogenations of alkynes and dienes in hydrocarbon streams. In connection with the present invention, the following publications in which the use of alumina as support material is disclosed are particularly relevant.

EP-A-0 064 301 describes a catalyst for the selective hydrogenation of acetylene, which consists of Pd which was modified with Ag; the support used is α-alumina. The Pd content is from 0.01 to 0.025% by weight and Ag is present in an amount which is from 2 to 10 times that of Pd. In the prepared catalyst, the silver is distributed over all catalyst particles while 90% of the palladium are present in an edge zone of 300 μm.

The two applications EP-A-0 686 615 and EP-A-0 780 155 describe a catalyst for the selective gas-phase hydrogenation of alkynes in the C2 or C3 stream. The catalyst is palladium to which a metal of group 11 was added. The support material used in each case is alumina. At least 80% of both metals are present in a zone which extends from the edge of the catalyst particle to a radius which is 80% of the external radius of the catalyst particle. The palladium content is from 0.01 to 0.5% by weight of the catalyst and the ratio of the metal of group 11 to palladium is from 0.05 to 0.4 (686 615) or from 0.4 to 3 (780 155). The preferred metal of group 11 in both applications is silver.

The German application with the file reference 198 39 459.4, filed on Aug. 28, 1998, (counterPart of U.S. Pat. No. 6,437,206) describes a catalyst for selective hydrogenation which contains at least one hydrogenationactive metal on an alumina support and, in the unused state, exhibits in the X-ray diffraction pattern reflections which correspond to the following interplanar spacings (in $10^{-10}$ m): 4.52, 2.85, 2.73, 2.44, 2.31, 2.26, 2.02, 1.91, 1.80, 1.54, 1.51, 1.49, 1.45 and 1.39, in each case with specific relative intensities. In a preferred embodiment, the hydrogenation-active metal is platinum and/or palladium, which is doped with copper and/or silver.

The German application with the file reference 198 40 373.9, filed on Sep. 3, 1998, (counterpart of U.S. Pat. No. 6,350,717) discloses a process in which unsaturated compounds in hydrocarbon streams are hydrogenated over a catalyst which contains at least one metal of the tenth group of the Periodic Table of the Elements and at least one metal of the eleventh group of the Periodic Table of the Elements on an alumina support, the metal or the metals of the tenth group being concentrated essentially in an edge layer close to the surface of the catalyst particle, the metal or the metals of the eleventh group being present distributed essentially uniformly over the volume of the catalyst particle, and the weight ratio of the metal or of the metals of the eleventh group to the metal or the metals of the tenth group being not more than 1.95.

All abovementioned publications disclose catalysts in which alumina is used as the support. There are only a few references which disclose selective hydrogenation catalysts which are applied to a support other than alumina.

Thus, DE-A-2 156 544 discloses a process for obtaining ethylene by selective catalytic gas-phase hydrogenation of acetylene in the C2 cut of the olefin preparation, a palladium catalyst which is applied to a silica support being used. The catalyst is modified by zinc.

However, this process has the disadvantage that the oligomer formation occurs to an extent which is too high for present-day requirements. Furthermore, the selectivity too is frequently insufficient and the addition of CO proves necessary.

EP-A-0 764 463 describes a selective hydrogenation catalyst which comprises palladium which was modified with a promoter metal of groups 1 and 2 of the Periodic Table. Here too, the catalyst is applied to a support based on silica.

Here too, the formation of oligomers and hence a reduction of the time-on-stream of the catalyst are frequently observed.

DE-P-31 19 850 describes a process which involves the selective hydrogenation of butadiene in a but-1-ene-containing C4 fraction. The catalyst used is applied to alumina or silica having a specific surface area of from 10 to 200 $m^2/g$, and the catalyst consists of a mixture of palladium and silver or compounds of these metals. The palladium content is from 0.05 to 5% by weight and the silver content is from 0.05 to 1% by weight. However, the catalyst described in this reference is suitable only for the selective hydrogenation of butadiene in C4 streams.

The German application with the file reference 198 40 372.0, filed on Sep. 3, 1998, (couterpart of U.S. Pat. No. 6,204,218) describes a catalyst which contains, in its active material, from 0.05 to 1.0% by weight of at least one metal or a compound of a metal of the tenth group of the Periodic Table of the Elements and from 0.05 to 1.0% by weight of at least one metal or a compound of a metal of the eleventh group of the Periodic Table of the Elements, the weight ratio of the metal of the eleventh group present to the metal of the tenth group present being from 0.95 to 1.05, and which contains, as a support, a silica-containing catalyst support having a BET surface area of from 2 to 400 $m^2/g$, at least 20% of the total pore volume of the catalyst being present in pores having a diameter above 100 nanometers. The catalyst is used for removing alkynes, dienes and/or monounsaturated hydrocarbons from material streams.

It may be said that it has not been possible so far to provide a selective hydrogenation catalyst for alkynes and dienes which is applied to a support material other than alumina, for example silica, and which has the same efficiency as catalysts applied to alumina as support material.

It is an object of the present invention to provide a catalyst for the selective hydrogenation of alkynes and dienes in C2-C5$^+$-olefin mixtures which is applied to a support other than alumina, but which is to have the same efficiency as those catalysts in which alumina was used as the support. Furthermore, such a catalyst should be very simple to prepare. Preferably, the catalyst should also be lighter than those catalysts in which alumina was used as the support material.

We have found that this object is achieved by a catalyst for the selective hydrogenation of alkynes and dienes in C2-C5$^+$-olefin mixtures, the catalyst containing (a) a metal of the tenth group of the Periodic Table,
(b) a metal of the eleventh group of the Periodic Table and
(c) if required, a compound of a metal of the first or second group of the Periodic Table, and these metals being applied to a support which is selected from the group consisting of silica, titanium dioxide, zirconium oxides, spinels, zinc aluminate, zinc titanate or mixtures thereof, and the metal of the eleventh group being distributed homogeneously over the cross section of the catalyst particle and the metal of the tenth group being concentrated in an edge layer close to the surface of the catalyst particle.

We have found that this object is furthermore achieved by a process for the preparation of such a catalyst, wherein the metal of the eleventh group is first homogeneously applied to the support and then the metal of the tenth group is applied. Preferably, the metal of the eleventh group is incorporated before the molding of the support, and the metal of the tenth group is preferably applied by impregnation with a solution of a salt of the respective metal.

Such a catalyst can advantageously be used in selective hydrogenations of alkynes and dienes in C2-C5$^+$-olefin mixtures. In connection with the present invention, olefin mixtures are preferably understood as meaning hydrocarbon streams, i.e. the products which are obtained on cracking mineral oil distillates or natural gas and which largely contain olefins. The novel process can however also be used for the selective hydrogenation of alkynes and dienes in olefin mixtures which were obtained in other processes known to those skilled in the art.

It has surprisingly been found that the selective application of the metal of the eleventh group and of the metal of the tenth group gives a selective hydrogenation catalyst for alkynes and dienes, which is applied to a support material which is not alumina. However, the catalyst obtained is just as efficient as those which are applied to an alumina support.

Suitable support material in the context of the present invention is in particular silica, with which it was possible to achieve the best results. Silica has the advantage of having a substantially lower specific gravity than alumina. Supported catalysts having a low bulk density are generally more economical than catalysts having a high bulk density. However, other support materials are suitable for use in a novel hydrogenation catalyst. These are, for example, titanium dioxide, zirconium oxides, zinc aluminate, zinc titanate or mixtures of said materials.

The support materials used in the present invention have a BET surface area of from 20 to 400, preferably from 100 to 160, $m^2/g$ and a pore volume of from 0.1 to 1.5, preferably from 0.7 to 1.2, ml/g.

The metal of the tenth group is present in amounts of from 0.005 to 1, preferably from 0.02 to 0.6, % by weight, based on the total mass, in the novel catalyst. It has been found that, among the metals of this group, i.e. nickel, palladium and platinum, the best results are achieved using palladium. The use of palladium is thus preferred.

The metal of the tenth group accumulates essentially in an edge layer close to the surface of the support. In general, more than 80, preferably more than 90, particularly preferably more than 95% by weight of the metal or of the metals are contained in a layer which has a thickness of not more than 0.6 mm and is bounded by the geometric surface of the catalyst particle. Preferably, this layer is not more than 0.45 mm thick.

An important element of the catalyst according to the present invention is the promoter metal, which is a metal from the eleventh group of the Periodic Table, i.e. copper, silver or gold. The addition of this metal and its specific arrangement in the hydrogenation catalyst according to the present invention permit the selective hydrogenation of alkynes and dienes with a high activity and selectivity. At the same time, the tendency to form oligomers and hence the resulting catalyst deactivation are reduced.

The metal of the eleventh group is present in amounts of from 0.005 to 1, preferably from 0.05 to 0.6% by weight, based on the total mass, in the novel catalyst. The ratio of metal of the eleventh group to metal of the tenth group is from 0.01 to 100, based on the metal of the tenth group. Preferably, this ratio is in a range from 0.5 to 30, particularly preferably from 1.5 to 20, in which the best results were achievable. It is furthermore preferred if the metal of the eleventh group is silver.

The catalyst according to the present invention may have a composition such that in each case only one metal of the eleventh group and one metal of the tenth group or compounds of these metals are present. However, it is also possible for two or more metals of the eleventh group and of the tenth group or compounds thereof to be present independently of one another in the catalyst.

It is particularly preferred if the catalyst according to the present invention contains palladium and silver.

The metal of the eleventh group is distributed over the entire cross section of the catalyst particle in the novel catalyst.

This can be achieved by methods known to those skilled in the art, such as the incipient wetness method, by impregnating the molded support. Preferably, the metal of the eleventh group is applied before the support is molded. For this purpose too, it is possible to use those methods known to those skilled in the art, such as impregnation of the precipitated support material with the metal of the eleventh group or a compound thereof, coprecipitation of the support compound and of the metal of the eleventh group or of a compound thereof, mixing of the support material with the metal of the eleventh group or a compound thereof in the dry or moist state, vapor deposition of the metal of the eleventh group onto the support material.

Thus, a support which contains the metal of the eleventh group homogeneously distributed over the support cross section is initially obtained.

In every case, the metal of the eleventh group is applied in a step which is carried out before the application of the metal of the tenth group. This metal of the tenth group can also be fixed on the support by the conventional measures known to those skilled in the art. Here too, however, it is once again preferred if this application is effected by impregnation with a solution of a suitable salt of the respective metal. This is preferably carried out in such a way that the solution is virtually completely absorbed by the pore volume of the support (incipient wetness method). However, the absorptivity of the support for the impregnating solution need not be fully exhausted, and the impregnating solution can therefore be used in an amount of less than 100%, for example not more than 95% by volume, not more than 90% by volume or not more than 85% by volume of the liquid volume absorbed by the support to be impregnated. The concentration of the salts in the solution is such that, after impregnation and conversion of the impregnated support into the finished catalyst, the components to be precipitated are present in the desired concentration on the catalyst. The salts are chosen so that they do not leave behind any residues which could present problems during the preparation of the catalyst or its subsequent use. In general, nitrates or ammonium salts are used.

It has been found that the novel desired distribution of the metal of the tenth group is achieved by the initially effected, homogeneous application of the metal of the eleventh group.

The novel catalysts may also contain further promoter metals which are selected from the first and second groups of the Periodic Table. Sodium, potassium, calcium and barium are preferably used. The application is effected by suitable methods known to those skilled in the art, for example by impregnation, simultaneously with the application of the metal of the tenth and of the eleventh group and independently of the chosen sequence of application.

After the application of the metals, the crude catalysts obtained are dried and calcined at the conventional temperatures, it being possible to carry this out in a single step or two separate steps. The drying is effected at from 50 to 250° C., preferably from 70 to 100° C. The calcination is carried out at from 250 to 700° C., preferably at from 300 to 650° C., it being possible to use, for example, rotating tubes, belt calciners or muffle furnaces. The moldings have the usual shape, for example extrudates, spheres, rings or pellets, and are prepared by, for example, pelleting or extrusion of the supports.

The novel catalysts are suitable for selective hydrogenation of generally all alkynes and dienes of 2 to 5 carbon atoms in mixtures of these with olefins, generally in hydrocarbon streams obtained on cracking. The hydrogenation can be carried out in the gas phase and in the liquid phase, analogously to known hydrogenation processes under heterogeneous catalysis. The hydrogenation can be carried out as a pure gas-phase process and also as a gas/liquid-phase process. These processes are known to those skilled in the art. The reaction parameters, for example hydrocarbon throughput, temperature and pressure, are chosen analogously to the known processes.

The amount of hydrogen used is from 0.8 to 5, preferably from 0.95 to 2, times the amount required stoichiometrically for complete reaction.

Examples of hydrogenation processes in which the novel catalyst can be used are mentioned below
- selective hydrogenation of acetylene in C2 streams to give ethylene (referred to below as process A)
- selective hydrogenation of propyne and/or propadiene in C3 streams to give propylene (process B)
- selective hydrogenation of 1-butyne, 2-butyne, 1,2-butadiene and/or vinylacetylene in C4 streams to give 1,3-butadiene, 1-butene, cis- and/or trans-2-butene (process C),
- selective hydrogenation of 1-butyne, 2-butyne, 1,2-butadiene, 1,3-butadiene and/or vinylacetylene in C4 streams to give 1-butene, cis- and/or trans-2-butene in the case of butadiene-rich C4 streams (crude C4 cut) or low-butadiene C4 streams (raffinate I)(process D)
- selective hydrogenation of unsaturated compounds and/or unsaturated substituents of aromatic compounds in $C5^+$ streams to give more highly saturated compounds and/or aromatic compounds with more highly saturated substituents (process E).

Process A is usually carried out as a one-stage or multi-stage gas-phase process with a space velocity of the gaseous C2 stream of from 500 to 10,000 $m^3/m^3 \cdot h$, based on the catalyst volume, at from 0 to 250° C. and from 0.01 to 50 bar.

Process B is usually carried out as a one-stage or multi-stage gas-phase process with a space velocity of the gaseous C3 stream of from 500 to 10,000 $m^3/m^3 \cdot h$, based on the catalyst volume, or as a gas/liquid-phase process with a space velocity of the liquid C3 stream of from 1 to 50 $m^3/m^3 \cdot h$, based on the catalyst volume, at from 0 to 180° C. and from 0.01 to 50 bar.

Process C is usually carried out as a gas/liquid-phase process with a space velocity of the liquid C4 stream of from 1 to 50 $m^3/m^3 \cdot h$, based on the catalyst volume, at from 0 to 180° C. and from 2 to 50 bar. Process C can be used, for example, as a selective front-end vinylacetylene hydrogenation before a butadiene extraction.

Process D is usually carried out as a one-stage or two-stage gas/liquid-phase process with a space velocity of the C4 liquid stream of from 0.1 to 60, preferably from 1 to 50, $m^3/m^3 \cdot h$, based on the catalyst volume, at a reactor inlet temperature of from 20 to 90° C., preferably from 20 to 70 ° C. and from 5 to 50, preferably from 10 to 30, bar. For example, the process is carried out in two stages, the butadiene content, which in typical C4 streams from steam crackers is from 20 to 80% by weight, based on the total stream, being reduced in the first stage to a content of from 0.1 to 20% by weight and in the second stage to the desired residual content of from a few ppm by weight to about 1% by weight. It is also possible to distribute the total reaction over more than two reactors, for example three or four. The individual reaction stages can be operated with partial recycling of the hydrocarbon stream, the reflux ratio usually being from 0 to 30. On carrying out process D, isobutene is retained essentially unchanged and can be separated from the C4 stream by known methods before or after process D is carried out. Process D can be used, for example, as a butadiene hydrogenation in the C4 stream (if butadiene is not to be recovered as the desired product) or as a selective tail-end vinylacetylene hydrogenation after the butadiene extraction from the C4 stream.

Process E is preferably carried out as a gas/liquid-phase process with a space velocity of the liquid C5+ stream of from 0.5 to 30 $m^3/m^3 \cdot h$, based on the catalyst volume, at from 0 to 180° C. and from 2 to 50 bar. Process E can be used, for example, for the selective hydrogenation of pyrolysis gasoline, for the selective hydrogenation of olefins in reformate streams or coke furnace condensates and for the hydrogenation of styrene to ethylbenzene.

By adding metals of the eleventh group, the support is preconditioned in the novel catalysts in such a way that the formation of oligomers during the hydrogenation is substantially reduced, in contrast to other hydrogenation catalysts applied to the same supports. The time-on-stream of the catalyst thus increases substantially.

Furthermore, the addition of CO as a selectivity-controlling agent, which is still frequently required, is also no longer necessary. In the novel catalysts, the hydrogenation-active metal of the tenth group can be provided even with large excesses of promoter metal of the eleventh group without a loss of activity during hydrogenation being observed.

The examples which follow illustrate the present invention.

EXAMPLE 1 (NOVEL CATALYST A)

A novel catalyst was prepared by preparing a silica support in extrudate form (4 mm extrudates, BET surface area from 120 to 140 $m^2/g$, pore volume from 0.8 to 0.95 ml/g) in such a way that silver in the form of silver nitrate was added in an amount of 0.05% by weight, based on the amount of $SiO_2$ used, to the edge mill material during the edge milling step. After the extrusion to give 4 mm extrudates, the support was calcined and was then impregnated with 0.025% by weight, based on the support material used, of palladium in the form of palladium nitrate at room temperature. The solution volume used corresponded to 90% of the water absorption of the support. The catalyst was dried at 80° C. and then calcined at 500° C.

EXAMPLE 2 (NOVEL CATALYST B)

A novel catalyst was prepared by preparing a silica support in extrudate form (4 mm extrudates, BET surface area from 120 to 140 $m^2/g$, pore volume from 0.8 to 0.95 ml/g) in such a way that silver in the form of silver nitrate was added in an amount of 0.2% by weight, based on the amount of $SiO_2$ used, to the edge mill material during the edge milling step. After the extrusion to give 4 mm extrudates, the support was calcined and was then impregnated with 0.06% by weight, based on the support material used, of palladium in the form of palladium nitrate at room temperature. The solution volume used corresponded to 90% of the water absorption of the support. The catalyst was dried at 80° C. and then calcined at 500° C.

COMPARATIVE EXAMPLE 1 (COMPARATIVE CATALYST C)

A comparative catalyst was prepared by impregnating an alumina support in extrudate form, having a BET surface area of 8 $m^2/g$, with a nitric acid-containing, aqueous solution of 0.045% by weight, based on the support material used, of silver in the form of silver nitrate and of 0.025% by weight, based on the support material used, of palladium in the form of palladium nitrate at room temperature (integral Ag/Pd ratio=6.7:1). The solution volume used corresponded to 90% of the water absorption of the support. The catalyst was dried at 80° C. and then calcined at 400° C.

COMPARATIVE EXAMPLE 2
(COMPARATIVE CATALYST D)

A further comparative catalyst was prepared similarly to Example 8 of the application DE 2156544, a catalyst containing 0.025% of palladium and 0.01% of zinc on a silica gel support in the form of a 4 mm extrudate being obtained.

EXAMPLE 3

Performance Test of Catalysts A to D

The catalysts A to D were tested in the selective hydrogenation of acetylene in a C2 stream containing about 1% of alkyne at 20 bar and a loading of 3000 l/h and with an 80% $H_2$ excess, based on the stoichiometric amount. The respective activity, measured with reference to the reaction temperature, stability, measured with reference to the deactivation rate of the reaction, and selectivity, measured with respect to the inclination to oligomer formation, were tested and compared. Table 1 shows the test results of catalysts A to D.

TABLE 1

| Catalyst | A | B | C | D |
|---|---|---|---|---|
| Bulk density | 470 | 470 | 1100 | 470 |
| Palladium [% by weight] | 0.025 | 0.06 | 0.025 | 0.025 |
| Ag/Pd ratio | 2 | 3.3 | 1.8 | — |
| CO addition for performance stabilization | not required | not required | not required | required |
| Reaction temperature [° C.] | 65 | 50 | 45 | 65 |
| Deactivation rate of the reaction [%/h] | −0.048 | −0.002 | −0.001 | −0.159 |
| Oligomer formation [g/h] | 0.024 | 0.012 | 0.014 | 0.051 |

The results obtained show that the addition of silver to the support gives improved catalysts with respect to all characteristics (A and B as compared with D). Furthermore, it is clear that the addition of silver to the supports makes it unnecessary to add CO for increasing the selectivity (A and B as compared with D) and that higher Ag/Pd ratios lead to less coking and a slower deactivation rate (A as compared with D). Moreover, a substantial increase in activity can be achieved by increasing the amount of palladium (A as compared with B and D).

Compared with catalyst C, catalyst A and in particular catalyst B are catalysts which are substantially lighter and hence more economical for the operator and exhibit very good performance corresponding to the prior art (catalyst C).

EXAMPLE 4

The novel catalysts E to U were obtained by the following method and with variation of the individual preparation parameters stated in Table 2:

A silver-doped $SiO_2$ support in the form of 4 mm extrudates was prepared by precipitating silica at pH 6 from an ammoniacal sodium waterglass solution by adding sulfuric acid, filtering off said silica from the aqueous phase, eliminating its conductivity by washing with water and spraying it to give a powder (bulk density, varying according to production, of from 350 to 450 g/l, water content about 25%). The spray-dried powder obtained was kneaded (i.e. treated in an edge mill) with water and with the addition of a defined amount, based on the solid material used, of silver in the form of aqueous silver nitrate solution for one hour to give an extrudable material. The material treated in the edge mill was molded to give 4 mm extrudates. The extrudates were dried at 120° C. and calcined at a defined temperature. A product having a BET surface area of from 110 to 160 $m^2/g$ and a bulk density of from 440 to 480 g/l was obtained. The exact surface area values and bulk densities are shown in Table 1.

This support material was then impregnated with an amount, defined on the basis of the support material used, of palladium in the form of aqueous palladium nitrate solution at room temperature with agitation. The solution volume used corresponded to 95% of the water absorption of the support. The material obtained was dried with admission of air at a defined temperature and with agitation and then calcined for 1 hour at a defined temperature with agitation. The exact preparation parameters are shown in Table 1.

Performance Tests of Catalysts E to U

The catalysts E to U were tested at 1 bar in a straight pass. The GHSV was 3000 l/h. The stream was composed of 1% by volume of acetylene in ethylene, and 1.8 equivalents, based on the amount of $C_2H_2$ used, of $H_2$ were added. The temperatures required for a 90% conversion of the acetylene and the selectivity values obtained are shown in Table 2.

TABLE 2

| Catalyst | E | F | G | H | I | J | K | L | M | N | O | P | Q | R | S | T | U |
|---|---|---|---|---|---|---|---|---|---|---|---|---|---|---|---|---|---|
| Palladium [% by weight] | 0.025 | 0.025 | 0.06 | 0.06 | 0.06 | 0.06 | 0.06 | 0.06 | 0.06 | 0.06 | 0.06 | 0.06 | 0.06 | 0.06 | 0.04 | 0.065 | 0.025 |
| Silver [% by weight] | 0.15 | 0.2 | 0.2 | 0.3 | 0.2 | 0.2 | 0.2 | 0.2 | 0.2 | 0.2 | 0.2 | 0.2 | 0.2 | 0.2 | 0.2 | 0.2 | 0.2 |
| Ag/Pd ratio | 6 | 8 | 3.33 | 5 | 3.33 | 3.33 | 3.33 | 3.33 | 3.33 | 3.33 | 3.33 | 3.33 | 3.33 | 3.33 | 5 | 3.1 | 8 |
| Support properties | | | | | | | | | | | | | | | | | |
| Calcination temperature [° C.] | 850 | 850 | 850 | 850 | 850 | 850 | 850 | 850 | 850 | 850 | 850 | 850 | 850 | 850 | 850 | 850 | 940 |
| Bulk density [g/l] | 470 | 430 | 430 | 400 | 470 | 470 | 470 | 470 | 470 | 470 | 470 | 470 | 470 | 470 | 470 | 470 | 470 |
| BET surface area [$m^2/g$] | 144 | 124 | 124 | 112 | 140 | 140 | 159 | 159 | 159 | 159 | 159 | 159 | 159 | 159 | 159 | 159 | 97 |
| Water absorption [ml/g] | 1.06 | 0.98 | 0.98 | 0.82 | 0.89 | 0.89 | 0.87 | 0.87 | 0.87 | 0.87 | 0.87 | 0.87 | 0.87 | 0.87 | 0.87 | 0.87 | 0.86 |
| Catalyst drying conditions | | | | | | | | | | | | | | | | | |
| Temperature [° C.] | 80 | 80 | 80 | 200 | 200 | 200 | 100 | 200 | 300 | 200 | 200 | 200 | 200 | 200 | 200 | 200 | 80 |
| Time [h] | 2 | 2 | 2 | 0.5 | 0.5 | 0.5 | 0.5 | 0.5 | 0.5 | 0.5 | 0.5 | 0.5 | 0.5 | 0.5 | 0.5 | 0.5 | 2 |
| Moist standing time until drying [h] | 0.5 | 0.5 | 0.5 | 0.5 | 0.5 | 188 | 0.5 | 0.5 | 0.5 | 0.5 | 0.5 | 0.5 | 0.5 | 0.5 | 0.5 | 0.5 | 0.5 |

TABLE 2-continued

| Catalyst | E | F | G | H | I | J | K | L | M | N | O | P | Q | R | S | T | U |
|---|---|---|---|---|---|---|---|---|---|---|---|---|---|---|---|---|---|
| Catalyst calcination conditions | | | | | | | | | | | | | | | | | |
| Temperature [° C.] | 360 | 500 | 500 | 500 | 500 | 500 | 500 | 500 | 500 | 300 | 350 | 400 | 450 | 500 | 500 | 500 | 500 |
| Performance test | | | | | | | | | | | | | | | | | |
| Temperature for 90% conversion [° C.] | 119 | 104 | 73 | 81 | 64 | 54 | 61 | 63 | 57 | 81 | 69 | 62 | 67 | 63 | 71 | 68 | 103 |
| Selectivity at 90% conversion [%] | 63 | 40 | 19 | 41 | 28 | 38 | 42 | 27 | 31 | 40 | 38 | 18 | 35 | 26 | 15 | 6 | 49 |

We claim:

1. A catalyst particle for the selective hydrogenation of alkynes and dienes in C2-C5+-olefin mixtures, comprising
   (a) palladium in an amount of from 0.005 to 1% by weight based on the total mass, and
   (b) silver in an amount of from 0.005 to 1% by weight based on the total mass,
   with (a) and (b) being applied to a silica support, silver being distributed homogeneously over the catalyst particle and palladium being present in an edge layer close to the surface of the catalyst particle.

2. The catalyst particle as claimed in claim 1 additionally comprising (c) a compound of a metal of the first or second group of the Periodic Table.

3. The catalyst particle as claimed in claim 1, wherein the amount of palladium is from 0.02 to 0.6% by weight.

4. The catalyst particle as claimed in claim 1, wherein the ratio of silver to palladium is from 0.01 to 100.

5. The catalyst particle as claimed in claim 4, wherein the amount of silver is from 0.05 to 0.6% by weight.

6. The catalyst particle as claimed in claim 4, wherein the ratio of silver to palladium ranges from 0.5 to 30.

7. The catalyst particle as claimed in claim 4, wherein the ratio of silver to palladium ranges from 1.5 to 20.

8. A process for the preparation of the catalyst particle as claimed in claim 1, wherein first silver is applied to the support in such a way that it is homogeneously distributed and then palladium is applied.

9. A process as claimed in claim 8, wherein the application of silver is effected before molding the support.

10. A process as claimed in claim 8, wherein the application of silver is effected after molding the support.

11. A process as claimed in claim 9, wherein silver is introduced by kneading into the support material during an edge milling step.

* * * * *